United States Patent [19]

Shimomura

[11] Patent Number: 4,622,126

[45] Date of Patent: Nov. 11, 1986

[54] ENGINE AIR/FUEL RATIO SENSING DEVICE

[75] Inventor: Setsuhiro Shimomura, Himeji, Japan

[73] Assignee: Mitsubishi Denki Kabushiki Kaisha, Tokyo, Japan

[21] Appl. No.: 650,495

[22] Filed: Sep. 14, 1984

[30] Foreign Application Priority Data

Sep. 17, 1983 [JP] Japan ................................ 58-171588

[51] Int. Cl.[4] ........................................... G01N 27/46
[52] U.S. Cl. .................................. 204/425; 204/426; 204/427; 204/406
[58] Field of Search ................................ 204/421–429, 204/406

[56] References Cited

U.S. PATENT DOCUMENTS

| 4,123,700 | 10/1978 | La Conti et al. | 204/426 |
| 4,272,329 | 7/1981 | Hetrick . | |
| 4,366,039 | 12/1982 | Uchida et al. | 204/406 |
| 4,381,224 | 4/1983 | Fate et al. | 204/1 S |
| 4,440,621 | 4/1984 | Kitahara et al. | 204/425 |
| 4,447,780 | 5/1984 | Youmans et al. | 204/406 |
| 4,472,247 | 9/1984 | Rohr et al. | 204/425 |
| 4,505,806 | 3/1985 | Yamada | 204/426 |
| 4,506,226 | 3/1985 | Luce et al. | 204/406 |

OTHER PUBLICATIONS

Engine Sensors: State of the Art (Fleming).
Oxygen Sensing by Electrochemical Pumping (Hetrick et al).

Primary Examiner—T. Tung
Attorney, Agent, or Firm—Leydig, Voit & Mayer, Ltd.

[57] ABSTRACT

An engine air/fuel ratio sensing device for measuring the oxygen partial pressure or concentration in the exhaust gas of an engine. The device has a sensor and a control circuit coupled to each other. The sensor consists of an electrolyte oxygen pump cell and an electrolyte oxygen sensor cell, both cells having a gap portion therebetween. The oxygen pump cell pumps oxygen into ambient gas when electrically energized. The sensor cell produces an electromotive force when there is an oxygen partial pressure difference thereacross due to the pumping of the pump cell. The control circuit has a differential amplifier which receives as an input the electromotive force for comparison with a predetermined reference voltage. The amplifier continuously provides an output, used for driving a pumping current through the pump cell, until the electromotive force reaches the reference voltage at which an equilibrium condition for the pumping current is established. The differential amplifier accomplishes this function with a series combination of a feedback resistor and a feedback capacitor.

5 Claims, 4 Drawing Figures

ENGINE AIR/FUEL RATIO SENSING DEVICE

BACKGROUND OF THE INVENTION

This invention relates to a device for measuring an oxygen concentration within an exhaust gas from an internal combustion engine etc., to sense the air/fuel ratio and in particular to an improved engine air/fuel ratio sensing device of an oxygen pump type constructed using an ion conductive solid electrolyte.

It is hitherto well known in the art to control e.g. the engine of an automobile to run at a stoichiometric (theoretical) air/fuel ratio, by sensing its combustion state in relation to the stoichiometric air/fuel ratio according to the variation of an electromotive force produced by the difference of the oxygen partial pressure between the exhaust gas and the atmosphere, by means of an oxygen sensor constructed with an ion conducting solid electrolyte such as stabilized zirconia. It is to be noted here that air/fuel ratio (A/F) is given by the weight ratio of air to fuel and that the principle of oxygen sensing is described in "Applied Physics Lett. 38(5), Mar. 1, 1981".

When the air/fuel ratio is the stoichiometric air/fuel ratio of 14.7, the above type oxygen sensor can provide a large output variation while outside the stoichiometric air/fuel ratio it provides a very low output variation. Therefore, when the engine is operated at an air/fuel ratio outside the stoichiometric air/fuel ratio, the output of such an oxygen sensor can not be utilized.

There has already been proposed an air/fuel ratio sensor of an oxygen pump type which eliminates such a disadvantage and enables the engine to be operated at any air/fuel ratio.

FIG. 1 shows an arrangement of an air/fuel ratio sensing device of an oxygen pump type, and FIG. 2 shows a cross sectional view of the sensor in FIG. 1 taken along line II—II, which is disclosed in a related application Ser. No. 606,926 filed May 4, 1984.

In FIG. 1, within an exhaust pipe 1 of an engine (not shown) an air/fuel ratio sensor, generally designated by a reference numeral 2, is disposed. This sensor 2 is formed of a solid electrolyte oxygen pump cell 3, a solid electrolyte oxygen sensor cell 4, and a supporting base 5. The solid electrolyte oxygen pump cell 3 includes an ion conducting solid electrolyte (stabilized zirconia) 6 in the form of a plate having platinum electrodes 7 and 8 disposed on the respective sides thereof. The solid electrolyte oxygen sensor cell 4, likewise the pump cell 3, includes an ion conductive solid electrolyte 9 in the form of a plate having platinum electrodes 10 and 11 disposed on the respective sides thereof. The supporting base 5 supports the oxygen pump cell 3 and the oxygen sensor cell 4 so that they are oppositely disposed having a minute gap "d" of about 0.1 mm therebetween.

An electronic control unit 12 is electrically coupled to the pump cell 3 and the sensor cell 4. More specifically, the electrode 10 is connected through a resistor R1 to the inverting input of an operational amplifier A the non-inverting input of which is grounded through a DC reference voltage source V. This DC reference voltage serves to control the output voltage of the sensor cell 4 to assume said voltage V according to the oxygen partial pressure difference between those within the gap and outside the gap. The electrode 7 is connected through a resistor R0 to the emitter of a transistor Tr whose collector is grounded through a DC power source B and whose base is connected to the output of the operational amplifier A and the inverting input of the operational amplifier A through a capacitor C. The electrodes 8 and 11 are grounded.

In operation, when the oxygen partial pressure within the gap portion between the cells 3 and 4 is the same as the oxygen partial pressure outside the gap portion, the sensor cell 4 generates no electromotive force. Therefore, the inverting input of the operational amplifier A receives no voltage and so the operational amplifier A provides as an output a maximum voltage corresponding to the reference voltage V to the base of the transistor Tr. Therefore, the transistor Tr is made conductive to cause a pump current Ip to flow across the electrodes 7 and 8 of the pump cell 3 from the voltage source B. Then the pump cell 3 pumps oxygen within the gap portion into the exhaust pipe 1. As a result, the sensor cell 4 develops an electromotive force thereacross according to the oxygen partial pressure difference on both sides of the cell 4.

Therefore, the oxygen sensor cell 4 applies an electromotive force "e" generated across the electrodes 10 and 11 to the inverting input of the operational amplifier A through the resistor R1. The operational amplifier A provides an output now proportional to the difference between the electromotive force "e" and the reference DC voltage V applied to the non-inverting input. The output of the operational amplifier A drives the transistor Tr to control the pump current Ip.

Thus, the electromotive force "e" approaches the reference voltage V. Accordingly, the control unit 12 reaches an equilibrium state and serves to provide a pump current Ip necessary for keeping the electromotive force "e" at the predetermined reference voltage V. The resistor R0 serves to provide an output corresponding to the pump current Ip supplied from the DC power source B as a pump current supply means. The pump current Ip corresponds to an air/fuel ratio value. This pump current Ip is converted into the voltage by the resistor R0 and is sent to a fuel control unit (not shown) so that the fuel control unit is controlled at a desired air/fuel ratio. The resistance of the resistor R0 is selected so as to prevent the pump current Ip from flowing excessively from the DC power source B. The capacitor C forms an integrator associated with the operational amplifier A and serves to make the electromotive force "e" precisely coincident with the reference voltage V.

One example of the static characteristics of a conventional air/fuel ratio sensing device of an oxygen pump type thus constructed in the form of a negative feedback control is shown in FIG. 3. The different characteristic curves a and b are obtained by changing the reference voltage V in FIG. 1, as disclosed in related application Ser. No. 606,910 filed May 4, 1984. The characteristic curve a is preferable when the air/fuel ratio (A/F) is controlled in a so-called "rich" region where the A/F ratio is below the stoichiometric A/F ratio 14.7 and in a so-called "lean" region where the A/F ratio is above the stoichiometric A/F ratio 14.7 while the characteristic curve b is preferable when the A/F ratio is controlled at the stoichiometric A/F ratio 14.7.

The air/fuel ratio sensor 2 illustrated in FIG. 1 has basically excellent characteristics because in either the rich region or the lean region the A/F ratio is linearly interrelated with the pump current Ip to thereby enable the engine to be operated at any A/F ratio.

However, even with the sensor 2 in FIG. 1, the oxygen pump cell 3 and the oxygen sensor cell 4 have at least an electrical first order lag, respectively. There is also a considerable lag time required for measured gas within the exhaust pipe 1 to disperse into the minute gap "d".

Furthermore, since the air/fuel ratio sensing device shown in FIG. 1 always requires a negative feedback control through an integrator in order to properly make the electromotive force "e" of the oxygen sensor cell 4 coincident with the reference voltage V, it has the following disadvantages in the dynamic characteristic range. These disadvantages are also present with, the device shown in Hetrick, U.S. Pat. No. 4,272,329 which includes an integrator formed by an operational amplifier and capacitor.

First of all, the response lag as an air/fuel ratio sensor is always high due to the integration by the integrator so that its performance as required for the A/F ratio control of an engine is not totally satisfactory.

Secondly, there is at least a phase lag of 180 degrees due to lag elements such as the oxygen pump cell 3 (90 degrees) and the sensor cell 4 (90 degrees) and in addition the phase lag of 90 degrees due to the integrator formed of the operational amplifier A and the capacitor C, with the result that the sensor 2 has a danger of oscillation. Some experiments have revealed that the combination of various parameters such as the flow temperature of measured gas or an A/F ratio often causes the sensor to oscillate.

SUMMARY OF INVENTION

It is an object of the invention to provide an air/fuel ratio sensing device of an oxygen pump type with good response and improved characteristics by eliminating the above disadvantages.

For this, briefly, the present invention has a differential amplifier the characteristics of which are formed by the addition of an integrator component and a gain component in the feedback circuit thereof.

More specifically, the present invention provides an engine air/fuel ratio sensing device including an air/fuel sensor and a control circuit coupled to the sensor. The air/fuel sensor has a gap portion for introducing the exhaust gas of the engine, a solid electrolyte oxygen pump cell for controlling the oxygen partial pressure within the gap portion, and a solid electrolyte oxygen sensor cell for producing an electromotive force corresponding to the difference between the oxygen partial pressure in the exhaust gas within the gap portion and the oxygen partial pressure in the exhaust gas outside the gap portion. The control circuit has an input portion for comparing a predetermined reference voltage with the electromotive force to continuously provide an output until the electromotive force reaches the reference voltage and an output portion for driving a pump current through the oxygen pump cell in response to the output of the input portion, the input portion having a transfer function of an amplifier component plus an integrator component. As a result, the air/fuel ratio of the engine is detected according to an output corresponding to the pump current.

The input portion comprises an input resistor one end of which is connected to one of the electrodes of the sensor cell, a differential amplifier the inverting input of which is connected to the other end of the input resistor and the non-inverting input to which is connected a source of the predetermined reference voltage, and a feedback series circuit consisting of a feedback resistor and a feedback capacitor, the feedback circuit being connected between the inverting input and the output of the differential amplifier. The transfer function is given by $R_2/R_1 + 1/sCR_1$, where $R_2$ represents the resistance of the feedback resistor, $R_1$ the resistance of the input resistor, s Laplacian, and C the capacitance of the feedback capacitor.

The output portion comprises a transistor whose base is connected to the output of the differential amplifier and whose collector is grounded through a DC power source, and a current limiting resistor connected between the emitter of the transistor and one of the electrodes of the pump cell, the voltage drop of the current limiting resistor being used as an output of the control circuit means for a fuel control.

BRIEF DESCRIPTION OF THE DRAWINGS

Throughout the figures, the same reference numerals indicate identical or corresponding portions.

DETAILED DESCRIPTION OF THE PREFERRED EMBODIMENT

One preferred embodiment of an air/fuel ratio sensing device for an engine in accordance with the present invention will now be described in detail with reference to the accompanying drawings, particularly FIG. 4.

Figure 1:
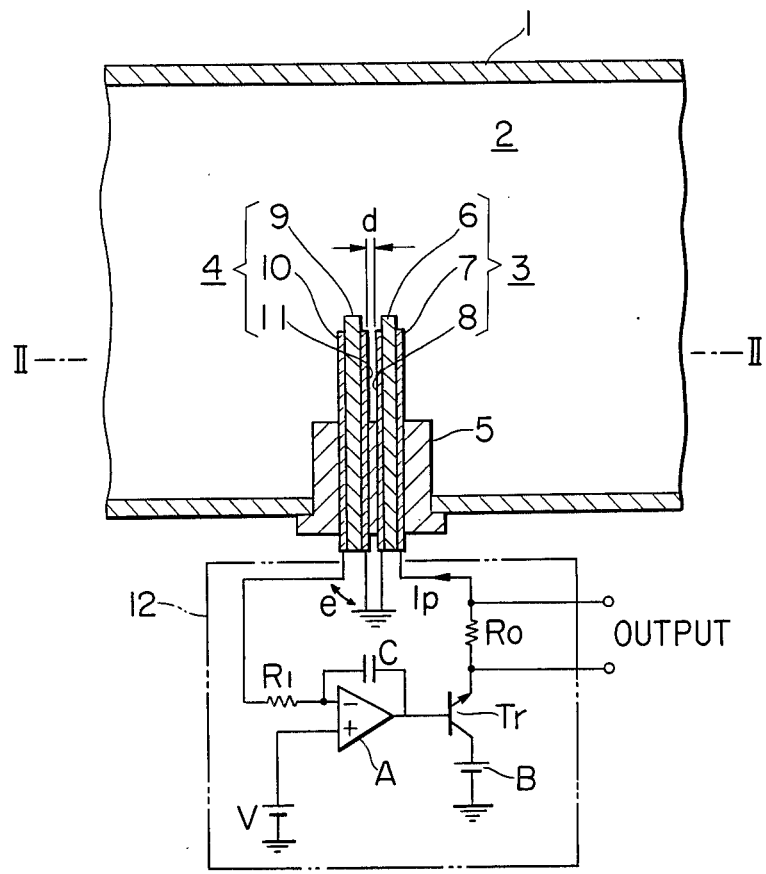
FIG. 1 shows an arrangement of an air/fuel ratio sensing device for an engine, associated with an exhaust pipe.
Figure 2:
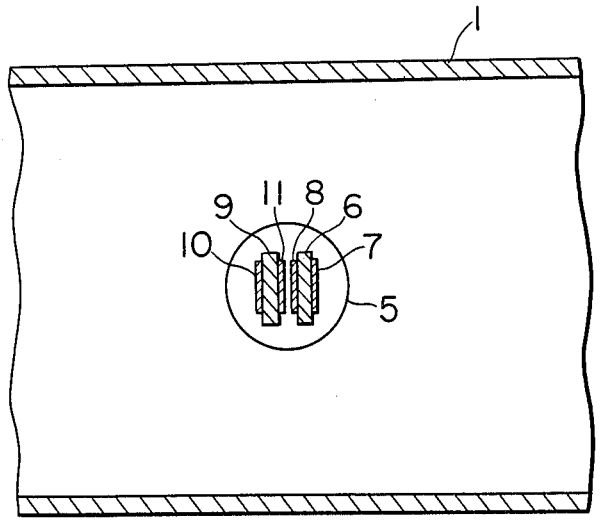
FIG. 2 shows a cross-sectional view of the sensor in FIG. 1, taken along line II—II.
Figure 3:
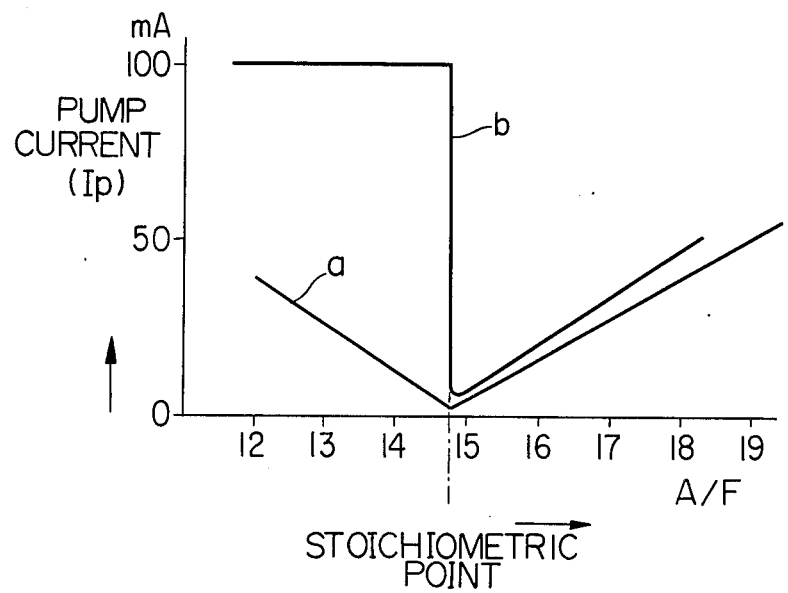
FIG. 3 shows characteristic curves of the sensing device in FIG. 1 wherein the ordinate axis denotes a pump current and the abscissa axis denotes an air/fuel (A/F) ratio.
Figure 4:
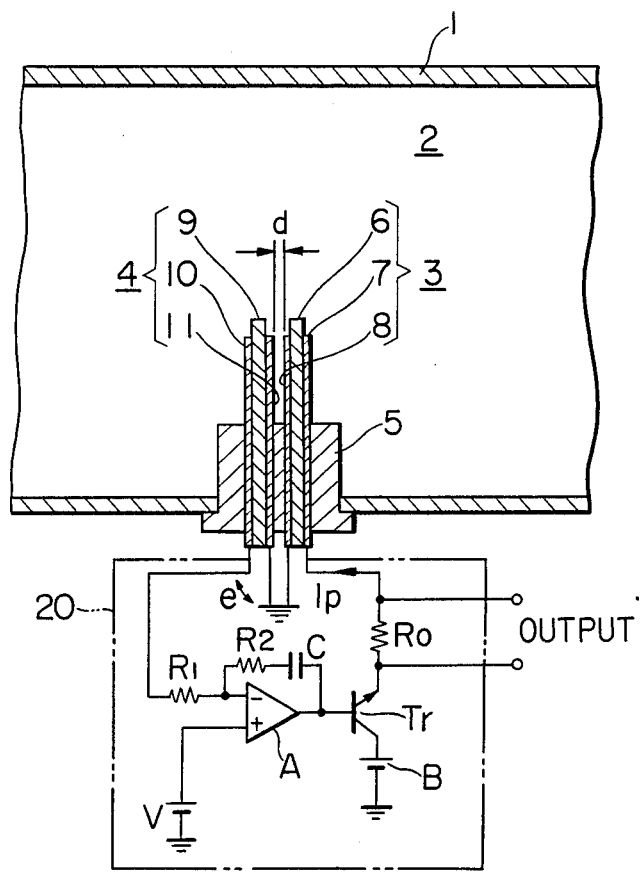
FIG. 4 shows an arrangement of an air/fuel ratio sensing device for an engine, associated with an exhaust pipe, in accordance with the present invention.

As seen from the comparison of the arrangements of FIGS. 4 and 1, they are different only in that the former has an electronic control circuit unit 20 including a resistor $R_2$ serially connected with the capacitor C in the feedback circuit of the operational amplifier A of the latter.

Therefore, the transfer function G of the circuit formed of the operational amplifier A, the resistors $R_1$ and $R_2$, and the capacitor C is given by the following equation:

$$G = R_2/R_1 + 1/sCR_1$$

where s represents Laplacian.

In this equation, the first term $R_2/R_1$ represents the voltage gain of the output to the input of the operational amplifier A, the output voltage being proportional to the input voltage which is the voltage difference of the electromotive force "e" of the oxygen sensor cell 4 and the reference voltage V. The second term $1/sCR_1$ represents the integrated value of the input voltage of the operational amplifier A. It is to be noted that the transfer function of the oxygen sensing device in FIG. 1 (disclosed in related application Ser. No. 606,926, filed May 4, 1984) is given by the second term alone.

Apparent from the above equation, the transfer function G approximates to $R_2/R_1$ in a higher frequency region of the electromotive force e, which includes an AC component superposed with a DC component, out of the sensor cell 4 while it approximates to $1/sCR_1$ in a lower frequency region thereof. Namely, in the lower frequency region of the electromotive force e, the control device according to the present invention serves as an integrator like the control device in FIG. 1 to properly control the voltage difference at the inputs of the operational amplifier A to zero, resulting in the above noted equilibrium state.

On the other hand, in the higher frequency region of the electromotive force "e" of the sensor cell 4, the control device in FIG. 4 provides a sufficiently high gain defined by R2/R1 and good response because it serves as a differential amplifier which has no phase lag.

Therefore, it is made possible to perform good control because of this good responsiveness if a sensing device according to the present invention as shown in FIG. 4 is employed for making an air/fuel ratio control for an engine.

Furthermore, since in the higher frequency region the sensing device according to the present invention is not required to function as an integrator requiring a phase lag of 90 degree, the phase lag in the higher frequency region no longer exceeds 180 degrees in a normal condition and so the sensing device according to the present invention has little danger of the above noted oscillation tendency. It is to be noted that experiments have shown that such an oscillation does not arise and good characteristics are provided in any possible combination of engine parameters such as flow rate, temperature, or air/fuel ratio of a measured gas.

In accordance with the present invention as stated above by the combination of an element sensing as an integrator of the characteristics of the differential amplifier with another element generating a proportional output voltage, an air/fuel ratio sensor can be achieved having the stabilized characteristics of good responsiveness, no loss of control for keeping the EMF of the oxygen sensor correctly following a predetermined reference voltage and further has no fear of oscillation. Also just by the addition of only one element (resistor R2) to the arrangement shown in FIG. 1, the desirable characteristics can be obtained extremely simply. Furthermore, it is also possible that the integrator be provided independently of the proportional amplifier and adding their respective outputs by an adder.

It will be appreciated by anyone of ordinary skill in the art that the invention should not be limited to the described and illustrated embodiment but various modifications are possible without departing from the spirit of the invention.

What I claim as a patent is:

1. An engine air/fuel sensing device comprising:
an air fuel sensor means having a gap portion for receiving an exhaust gas of said engine, a solid electrolyte oxygen pump cell for controlling an oxygen partial pressure within said gap portion, and a solid electrolyte oxygen sensor cell for producing an electromotive force corresponding to the difference between the oxygen partial pressure in the exhaust gas within said gap portion and the oxygen partial pressure in the exhaust gas outside said gap portion; and control circuit means coupled to said sensor means including an input portion for comparing a predetermined reference voltage with the electromotive force to continuously provide an output until the electromotive force reaches the reference voltage, said input portion comprising an input resistor having one end connected to an electrode of said sensor cell, a differential amplifier having an inverting input connected to the other end of said input resistor and a non-inverting input connected to a source of said predetermined reference voltage, an output portion for driving a pump current through said oxygen pump cell in response to the output of said input portion, and means coupling said output to said input portion having a transfer function of an amplifier component plus an integrator component, whereby the air/fuel ratio of the engine is detected according to an output corresponding to the pump current, said coupling means including a feedback series circuit consisting of a feedback resistor and a feedback capacitor, said feedback circuit being connected between the inverting input and the output of the differential amplifier.

2. An engine air/fuel ratio sensing device as claimed in claim 1 wherein said transfer function is given by $R2/R1 + 1/sCR1$, where R2 represents the resistance of said feedback resistor, R1 the resistance of said input resistor, s Laplacian, and C the capacitance of said feedback capacitor.

3. An engine air/fuel ratio sensing device as claimed in claim 1 wherein said output portion comprises a transistor having a base connected to the output of said differential amplifier and a collector grounded through a DC power source, and a current limiting resistor connected between the emitter of said transistor and an electrode of said pump cell, the voltage drop of said current limiting resistor being used as an output of said control circuit means for a fuel control.

4. An engine air/fuel ratio sensing device as claimed in claim 3, further comprising a base for supporting said pump cell and said sensor cell so that both cells project into an exhaust pipe having said gap portion.

5. An engine air/fuel ratio sensing device as claimed in claim 4 wherein said solid electrolyte comprises a stabilized zirconia.

* * * * *